United States Patent [19]

West et al.

[11] Patent Number: 5,318,525

[45] Date of Patent: Jun. 7, 1994

[54] STEERABLE ELECTRODE CATHETER

[75] Inventors: Scott West, Tracy; Richard Jaraczewski, Livermore, both of Calif.

[73] Assignee: Medtronic CardioRhythm, San Jose, Calif.

[21] Appl. No.: 866,383

[22] Filed: Apr. 10, 1992

[51] Int. Cl.$^5$ .............................................. A61M 37/00
[52] U.S. Cl. ...................................... 604/95; 128/772; 607/122
[58] Field of Search ......................... 604/96, 281, 282; 128/772, 657, 642, 786, 790, 800

[56] References Cited

U.S. PATENT DOCUMENTS

| | | |
|---|---|---|
| 3,470,876 | 10/1969 | Barchilon . |
| 3,552,384 | 1/1971 | Pierie et al. ............................ 604/95 |
| 3,605,725 | 9/1971 | Bentov . |
| 3,625,200 | 12/1971 | Muller .................................. 604/95 |
| 3,773,034 | 11/1973 | Burns et al. ........................... 604/95 |
| 4,277,168 | 7/1981 | Oku . |
| 4,685,457 | 8/1987 | Donenfeld . |
| 4,723,936 | 2/1988 | Buchbinder et al. .................. 604/95 |
| 4,753,223 | 6/1988 | Bremer . |
| 4,769,006 | 9/1988 | Papantonakos ..................... 128/786 |
| 4,826,087 | 5/1989 | Chinery . |
| 4,838,859 | 6/1989 | Strassman . |
| 4,874,371 | 10/1989 | Comben et al. . |
| 4,886,067 | 12/1989 | Palermo . |
| 4,944,727 | 7/1990 | McCoy . |
| 4,960,134 | 11/1990 | Webster, Jr. . |
| 4,998,916 | 3/1991 | Hammerslag et al. . |
| 5,055,109 | 10/1991 | Gould et al. .......................... 604/95 |
| 5,060,660 | 10/1991 | Gambale et al. ..................... 128/772 |
| 5,106,381 | 4/1992 | Chikama ............................... 604/95 |
| 5,125,896 | 6/1992 | Hojeibane ............................. 604/95 |
| 5,176,126 | 1/1993 | Chikama ............................... 604/95 |
| 5,254,088 | 10/1993 | Lundquist et al. ................... 128/772 |

FOREIGN PATENT DOCUMENTS

| | | |
|---|---|---|
| 0476807 | 3/1992 | European Pat. Off. . |
| 1213571 | 3/1966 | Fed. Rep. of Germany ........ 604/95 |
| 3714492 | 12/1987 | Fed. Rep. of Germany . |
| 90734 | 11/1937 | Sweden ................................. 604/95 |
| 0882477 | 11/1961 | United Kingdom ................. 604/95 |
| 1046478 | 10/1966 | United Kingdom ................. 604/95 |

*Primary Examiner*—John D. Yasko
*Assistant Examiner*—Anthony Gutowski
*Attorney, Agent, or Firm*—Townsend & Townsend Khourie & Crew

[57] ABSTRACT

A steerable catheter suitable for radiofrequency ablation of cardiac tissue comprises a catheter shaft with a deflectable tip at the distal end of the shaft. The tip is deflected by means of a shapable handle coupled to pull wires fastened to the distal end of the deflectable tip. A core wire extends from the handle to the distal tip, providing fine positioning of the deflectable tip by applying torque through the core wire to the tip. A spring tube is further provided in the deflectable tip for improved torque transmission and kink-resistance. The catheter has an electrode at the distal end of the deflectable tip for positioning at a target site and applying RF power to accomplish ablation.

48 Claims, 6 Drawing Sheets

STEERABLE ELECTRODE CATHETER

The present application is related to co-pending application Ser. Nos. 07/866,763, 07/867,241 and 07,866,683, filed on the same date as the present application. The disclosures of all of these co-pending applications are incorporated herein by reference.

BACKGROUND OF THE INVENTION

The present invention relates generally to the field of electrophysiology. More particularly, this invention relates to methods and apparatus for treating cardiac arrhythmias.

Symptoms of abnormal heart rhythm are generally referred to as cardiac arrhythmias, with an abnormally slow rhythm being classified as a bradycardia and an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of one of the chambers of the heart. The heart includes a number of normal pathways which are responsible for the propagation of signals necessary for normal electrical mechanical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVT's originate in the atria and are typically caused by an accessory pathway.

Treatment of both ventricular and supraventricular tachycardias may be accomplished by a variety of approaches, including drugs, surgery, implantable pacemakers/defibrillators, and catheter ablation. While drugs may be the treatment of choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radiofrequency electrical energy, laser energy, and the like.

Of particular interest to the present invention are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue in order to ablate a region of the tissue which forms part of arrhythmogenic site or the accessory pathway. By successfully destroying that tissue, the abnormal signalling patterns responsible for the tachycardia cannot be sustained. A method and system for performing RF ablation by controlling temperature at the ablation site is described in co-pending application Ser. No. 866,683, entitled "Method and System for Radiofrequency Ablation of Cardiac Tissue," the full disclosure of which is hereby incorporated herein by reference.

Catheters utilized in radiofrequency ablation are inserted into a major vein or artery, usually in the neck or groin area, and guided into the chambers of the heart by appropriate manipulation through the vein or artery. The tip of the catheter must be manipulable by the user from the proximal end of the catheter, so that the distal electrode can be positioned against the tissue region to be ablated. The catheter must have a great deal of flexibility in order to follow the pathway of the major blood vessels into the heart, and the catheter must permit user manipulation of the tip even when the catheter is in a curved and twisted configuration. Because of the high degree of precision required for proper positioning of the tip electrode, the catheter must be manipulable with a high degree of sensitivity and controllability. In addition, the distal portion of the catheter must be sufficiently resilient in order to be positioned against the wall of the ventricle and maintained in a position during ablation without being displaced by the movement of the beating heart. Along with the steerability, flexibility and resiliency, the catheter must have a sufficient degree of torsional stiffness to permit user manipulation from the proximal end.

Steerable catheters are known for use in a variety of medical procedures. See, for example, U.S. Pat. No. 4,998,916 to Hammerslag, U.S. Pat. No. 4,944,727 to McCoy, U.S. Pat. No. 4,838,859 to Strassmann, U.S. Pat. No. 4,826,087 to Chinery, U.S. Pat. No. 4,753,223 to Bremer, U.S. Pat. No. 4,685,457 to Donenfeld, U.S. Pat. No. 3,605,725 to Bentov, U.S. Pat. No. 3,470,876 to Barchilon and U.S. Pat. No. 4,960,134 to Webster, Jr. Typically, such catheters employ a plurality of steering wires, usually three or four, extending from a steering mechanism at the proximal end of the catheter to an anchor point at the distal end of the catheter. By tensioning certain of the steering wires using the control mechanism, the tip of the catheter can be manipulated in a desired direction. See, e.g., U.S. Pat. 3,470,876 to Barchilon or U.S. Pat. No. 3,605,725 to Bentov. In addition to being steerable in the lateral direction, further positioning of known catheters is accomplished by rotating the catheter as a whole about its longitudinal axis, typically by turning or twisting the proximal end of the catheter. This exerts a torque along the length of the catheter which is translated into a rotational motion at the distal end, allowing a laterally deflected distal tip to be rotated.

While radiofrequency ablation using existing catheters has had promising results, such catheters suffer from certain disadvantages. In particular, known catheters lack a sufficient degree of steering sensitivity to accurately position the distal tip electrode at the desired position within the heart. The known technique of achieving rotation of the distal tip by twisting the proximal end of the catheter frequently results in "whipping" of the distal tip in an abrupt and uncontrolled recoiling motion. Such recoiling can occur at unpredictable locations and timings, reducing the success of ablation procedures and potentially risking the health of the patient. Known catheters further suffer from the inability to maintain the position of the distal electrode against the wall of the ventricle the movement of the beating heart.

In addition, known catheters suffer from a tradeoff between catheter length and torsional stiffness, with catheters of relatively long length having insufficient torsional stiffness to allow effective positioning by rotating the proximal end of the catheter.

For these and other reasons, it would be desirable to provide a catheter suitable for radiofrequency ablation which is steerable from the proximal end with greater sensitivity and controllability than in known catheters. Further, the catheter should have greater torsional stiffness per unit length than known catheters, so that the relatively long catheters required in certain ablation procedures are sufficiently manipulable from the proximal end. At the same time, such catheters should allow both lateral and rotational manipulation of the distal tip for both "rough" and "fine" positioning. Further, the catheter should have sufficient flexibility to follow the contours of the vessel pathway into the heart without detracting from the catheter's steerability.

SUMMARY OF THE INVENTION

The present invention provides an improved steerable catheter which, in one embodiment, relies on a core wire extending from a proximal end of the catheter to a distal tip, the core wire providing a mechanism for fine rotational positioning of the tip electrode, and, at the same time, improving the torsional stiffness of the catheter. In this embodiment, the steerable catheter comprises a catheter shaft having a distal end, a proximal end, and a central lumen extending therebetween, wherein a distal portion of the shaft is deflectable; means extending from the proximal end to the distal end for deflecting the distal portion of the shaft about a transverse axis; a core wire extending through the central lumen and attached to the distal end of the shaft; and means for applying torque to a proximal end of the core wire to deflect the distal portion of the shaft about its longitudinal axis. The core wire is preferably tapered to have a gradually reduced diameter in the distal direction. Such a tapered profile decreases the bending stiffness at the distal end of the catheter, which is particularly desirable in the deflectable portion of the shaft.

In further embodiments, the steerable catheter will have at least one electrode at the distal end of the shaft which is connected to an external radiofrequency generator, so that the catheter may be used for radiofrequency ablation. The catheter may further include additional electrodes on the shaft located proximally of the distal electrode, the additional electrodes being connected to external monitoring equipment, for example, EKG machines or other monitoring and mapping equipment.

In an exemplary embodiment, the means for deflecting the distal portion of the catheter comprises at least three pull wires which are attached to radially offset locations at the distal end of the deflectable portion of the shaft, and means at the proximal end of the shaft for selectively applying tension to the pull wires to cause deflection of the deflectable portion.

Usually, the distal portion of the shaft includes at least three radially offset lumens, the pull wires being disposed in the central lumen of the catheter shaft over a proximal portion thereof and disposed in the radially offset lumens over the distal portion thereof.

Usually, the means for selectively applying tension comprises a shapable handle, and the means for applying torque to the core wire comprises a rotatable ring disposed on the handle, the ring being coupled to the proximal end of the core wire. A variety of other tension applying mechanisms, such as joy sticks, may also be employed.

In order to provide increased torsional rigidity to the catheter shaft, the shaft preferably comprises a polymeric tube having a durometer in the range from 45D to 95D, usually from 60D to 75D. Preferably, the shaft will have a composite structure including a base layer of a relatively high durometer material, e.g., polyimide; a stiffening layer, e.g., metal braid or coil, and an outer layer comprising the polymeric tube.

In a further embodiment, the steerable catheter includes a spring tube disposed coaxially in the central lumen of the deflectable tip and extending into the central lumen of the catheter shaft. The spring tube may be, for example, a polyimide tube in the central lumen of the deflectable tip extending partially into the distal end of the shaft. The polyimide tube provides a resilient backbone for the steerable tip, greatly improving torque transmission and kink-resistance.

In yet another aspect of the present invention, the core wire of the steerable catheter provides for a uniform, controlled bending of the distal tip. Thus, certain embodiments of the catheter need not comprise means for applying torque to the promixal end of the core wire, and the core wire need not extend the entire length of the catheter shaft (and instead may be anchored at some point proximal to the distal end of the shaft).

In a still further aspect of the present invention, the catheter includes an electrically and thermally insulating plate between the distal electrode tip and the catheter shaft. The plate provides a mechanical anchor for the pull wires as well as both electrical and thermal isolation of the electrode. Such electrical and thermal isolation is a particular advantage in protecting the shaft from damage from heat generated during use.

The invention further provides a method for positioning an electrode within a heart chamber, the method comprising the steps of percutaneously introducing the distal end of a catheter through the aorta or other blood vessel to the heart chamber, wherein the electrode is disposed at the distal end of the catheter; rotating the catheter and deflecting the distal end of the catheter about a transverse axis to position the electrode near a target site on an interior wall of the heart chamber; and applying rotational torque to a proximal end of a core wire which extends through a central lumen of the catheter and is attached to the distal end of the catheter, whereby the distal end of the catheter is deflected about a longitudinal axis to further position the electrode near the target site.

The method and apparatus of the present invention have several significant advantages over known catheter ablation techniques. In particular, the core wire of the steerable catheter provides a significant improvement in rotational steerability. After roughly positioning the distal electrode by manipulating the steering wires and rotating the proximal end of the catheter, the treating physician can controllably and precisely position the electrode at the desired location by applying torque to the core wire using the torque applying means, such as a rotatable ring disposed on the handle. Further rotational positioning benefits are obtained by the polyimide tubing construction of the catheter, which contributes to the increased torsional rigidity of the catheter. This increased rigidity, in combination with the rotational steerability provided by the core wire, substantially eliminates the "whipping" problems associated with known catheters. Further, the improved catheter maintains sufficient rigidity over a substantially longer length than catheters of previous construction. At the same time, the improved catheter is sufficiently flexible and manipulable to follow the contours of veins or arteries into the heart.

The invention and objects and features thereof will be more readily apparent from the following detailed description and appended claims when taken with the drawings.

DETAILED DESCRIPTION OF THE ILLUSTRATIVE EMBODIMENTS

Figure 1:
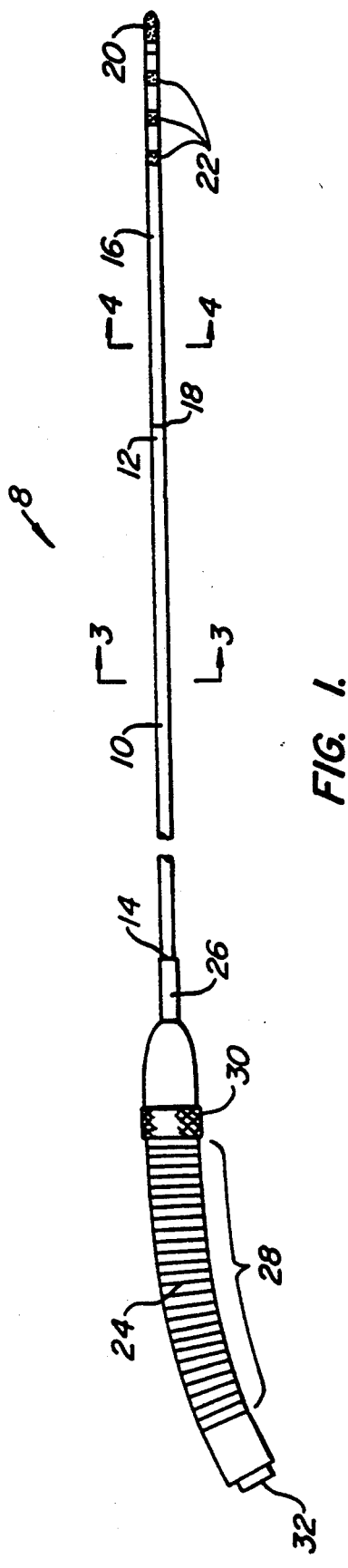
FIG. 1 is a front elevational view of the steerable catheter constructed in accordance with the principles of the present invention.
Figure 2:
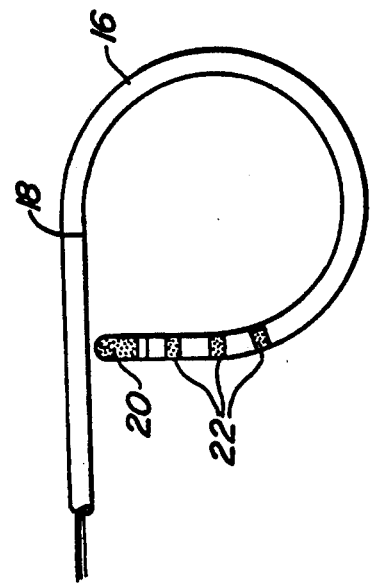
FIG. 2 is a front elevational view of the distal portion of the catheter of FIG. 1.

Referring to FIG. 1, a steerable catheter 8 constructed in accordance with the principles of the present invention comprises a shaft 10 having a distal end 12 and proximal end 14. A tip section 16 is fused at butt joint 18 to distal end 12 of shaft 10. A tip electrode 20 is mounted at the distal end of tip section 16, with band electrodes 22 disposed on tip section 16 proximally of tip electrode 20. A thermocouple (not shown) is located in the distal end of the tip section 16 and in thermal contact with the tip electrode 20. Proximal end 14 of shaft 10 is mounted to handle 24 through strain relief 26. Handle 24 includes a shapable body 28 in a middle portion thereof. A torque ring 30 is disposed about handle 24 distally of shapable body 28, as shown in FIG. 1, or proximally thereof. At the proximal end of handle 24 is electrical connector 32 for connecting tip electrode 20, band electrodes 22 and the thermocouple to RF power, mapping, and/or temperature measuring equipment. Tip section 16, as illustrated in FIG. 2, is flexible and laterally deflectable into various configurations using shapable handle 24. Preferably, tip section 16 can be deflected by at least 270° from the straight, distally-pointing configuration of FIG. 1 (as illustrated in FIG. 2).

Figure 3:
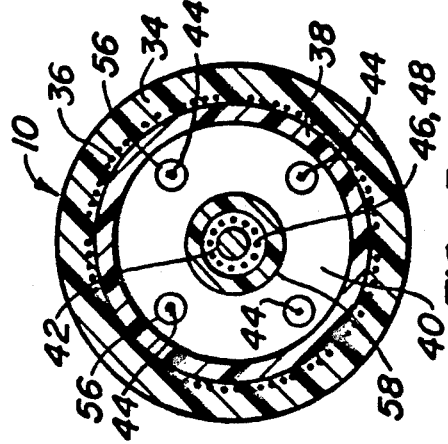
FIG. 3 is a cross-sectional view of the catheter body taken along line 3—3 of FIG. 1.
Figure 5:
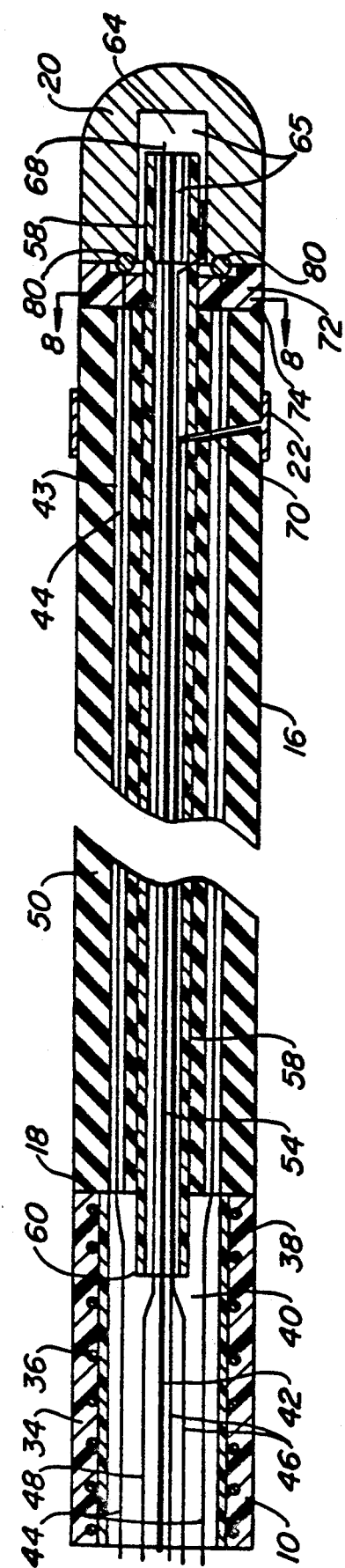
FIG. 5 is a front cross-sectional view of the distal tip of the catheter of FIG. 1.

Referring now to FIGS. 1, 3 and 5, shaft 10 comprises an outer jacket 34, which may be nylon, urethane or other plastic. Outer jacket 34 surrounds stiffener 36, (not shown in FIG. 3) which usually comprises a stainless steel braid or coil. The stiffener 36 is disposed about a base layer 38, which preferably comprises a tube of polyimide or other relatively stiff, high durometer material. The stiffness and torqueability characteristics of the shaft can be varied by varying the type of material used for outer jacket 34, stiffener 36 and base layer 38, as well as by using different geometries for the stiffener 38. For example, the stiffener 36 could be a braid or a coil, where the number of filaments, shape of filaments, coiling or weaving pattern, number of turns, and the like, can be varied individually or in combination to provide a desired stiffness. Preferably, the polyimide tube of base layer 38 has a thickness in the range from 0.002 in to 0.005 in.

Outer jacket 34, stiffener 36 and base layer 38 define a central lumen 40 extending the length of shaft 10. Disposed in central lumen 40 are a core wire 42, pull wires 44, electrode wires 46 and thermocouple wires 48.

Figure 4:
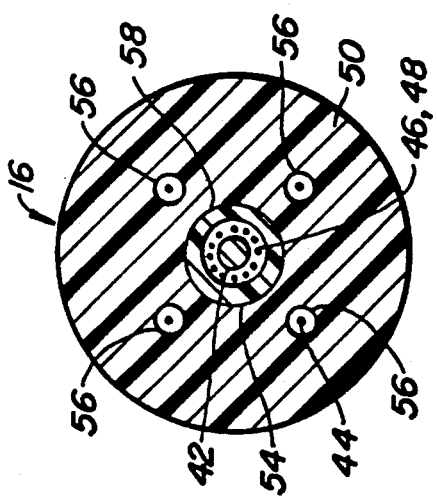
FIG. 4 is a cross-sectional view of the distal portion of the catheter taken along line 4—4 of FIG. 1.

Referring now to FIGS. 1, 4 and 5, tip section 16 comprises tubing 50 of a low durometer flexible plastic, such as Pebax TM, silicone rubber, or other resilient material. Preferably, tip section 16 has a durometer in the range of 30A to 60D. Tubing 50 usually has at least four lumens extending its length in parallel to its longitudinal axis, a central lumen 54 and at least three radially offset lumens 56 (with four being illustrated). Core wire 42 extends through central lumen 54, along with electrode wires 46 and thermocouple wires 48. Pull wires 44 (not shown in FIGS. 3 and 4) extend from the central lumen of shaft 10 to the radially offset lumens 56 of tip section 16. For purposes of clarity, electrode wires 46, thermocouple wires 48 and pull wires 44 are not shown in FIGS. 3 and 4.

A spring tube 58 is also disposed in central lumen 54 of tip section 16, the spring tube 58 fitting snugly against the walls of inner lumen 54 and having a hollow center through which core wire 42, electrode wires 46 and thermocouple wires 48 extend. Spring tube 58 usually comprises a polyimide tube which provides lateral and torsional stiffness as well as kink-resistance to tip section 16. The spring tube 58 could also be a braided or coiled structure, or a composite of multiple layers.

Referring now particularly to FIG. 5, tip section 16 is fixed to shaft 10 at butt joint 18, preferably by heat welding. Central lumen 54 of tip segment 16 is of smaller diameter than central lumen 40 of shaft 10, with spring tube 58 extending a distance, typically about 0.5 in., into the central lumen 40 of shaft 10. Such extension serves to limit kinking at or near butt joint 18 when tip section 16 is deflected. A proximal end 60 of the spring tube 58 will extend into central lumen 40, thereby enhancing the stiffness at the transition between the tip section 16 and the remainder of the shaft 10.

Core wire 42, electrode wires 46 and thermocouple wires 48 extend from central lumen 40 of shaft 10 into central lumen 54 of tip section 16 through the center of spring tube 58. At the distal end of tip section 16, spring tube 58 emerges from central lumen 54 into an aperture 64 within tip electrode 20. RF power wire 66 (one of electrode wires 46) is coupled to tip electrode 20. Thermocouple wires 48 terminate in a thermocouple 68 disposed within aperture 64. Preferably, aperture 64 is filled with high temperature adhesive to maintain thermocouple 68 in position. Electrode band wires 70 exit central lumen 54 within spring tube 58 and couple to band electrodes 22. Core wire 42 extends through central lumen 54 into aperture 64 of tip electrode 20.

Figure 8:
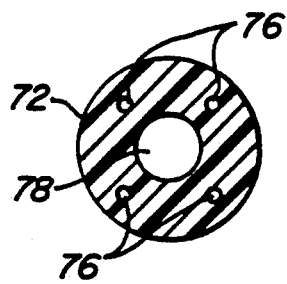
FIG. 8 is a front view of the anchor plate of the catheter of FIG. 1.

An electrically and thermally insulating anchor plate 72 is bonded to distal end 74 of tubing 50, tip electrode 20 being bonded to the distal side of anchor plate 72. Anchor plate 72, as shown in FIG. 8, has a central passage 78 corresponding to central lumen 54 of tip section 16, and four radially offset apertures 76 through which pull wires 44 pass. Referring again to FIG. 5, pull wires 44 terminate in anchors 80, which usually comprise steel balls formed on or welded to ends of pull wires 44. The anchors 80 are of larger diameter than apertures 76, providing a strong, pivotal connection between pull wires 44 and the distal end of tip section 16. Anchor plate 72 serves several functions. First, it protects the catheter body from thermal damage during ablation, allowing for many RF applications without catheter degradation. Secondly, it provides a strong component to which the pull wires 44 can be attached, without reliance on adhesive. Third, anchor plate 72 provides a means of electrically insulating the pull wires 44 from tip electrode 20, preventing the RF current from traveling back up the catheter to the handle assembly. The anchor plate may be formed from any polymeric or ceramic material having the necessary mechanical strength and electrical and thermal insulating properties. Preferred is the use of polyether ether ketone, available from ICI Americas, Inc., Wilmington, Del., under the tradename Victrex.

Figure 6:
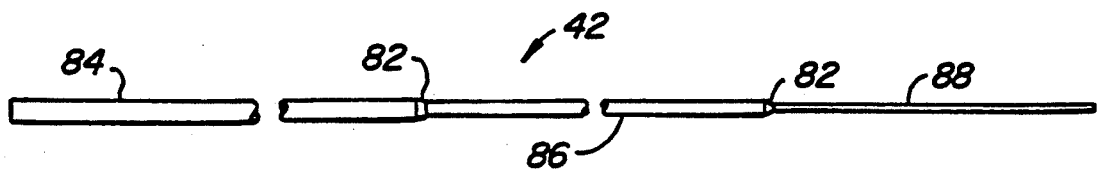
FIG. 6 is a front elevational view of the core wire of the catheter of FIG. 1.
Figure 7:
FIG. 7 is a front elevational view of a pull wire of the catheter of FIG. 1.

Referring now to FIG. 6, core wire 42 is usually stainless steel, and is tapered, typically being ground in three sections of different diameter separated by tapered transition sections 82. Proximal shaft portion 84 has the largest diameter, to provide the greatest stiffness both laterally and torsionally to the proximal portion of shaft 10 of the catheter. Distal shaft section 86 has an intermediate diameter, providing significantly more flexibility than that of the proximal shaft section 84 so as to allow deflection of the corresponding distal portion of shaft 10 of the catheter. Distal portion 88 of core wire 42 is of the smallest diameter, lending the highest degree of flexibility to tip section 16. The graduated diameters of the core wire permit deflection of tip section 16 at a constant or near constant radius. Core wire 42 further provides a structural member continuous from the proximal end to the distal end of the catheter having a significant degree of torsional stiffness. The taper profile of the core wire 42 may of course be varied to obtain any of a variety of tip shapes.

In addition to controlled flexibility, the core wire can provide an alternate means for transmitting torque to the catheter tip. By coupling the core wire to a rotatable ring on the handle of the catheter, as described below, torque can be applied to the distal tip of the catheter without having to rotate the entire handle assembly. The core wire further permits greater controllability and sensitivity in rotational positioning of tip electrode 20 than is afforded by turning the entire handle and catheter assembly.

Usually, pull wires 44 are stainless steel coated with a low friction plastic such as polytetrafluoroethylene (available from DuPont under the tradename Teflon ®). Electrode wires 46 are usually nickel for increased tensile strength but could be copper or other electrically conductive metals. Thermocouple wires 48 are usually copper and constantan, respectively.

Figure 9:
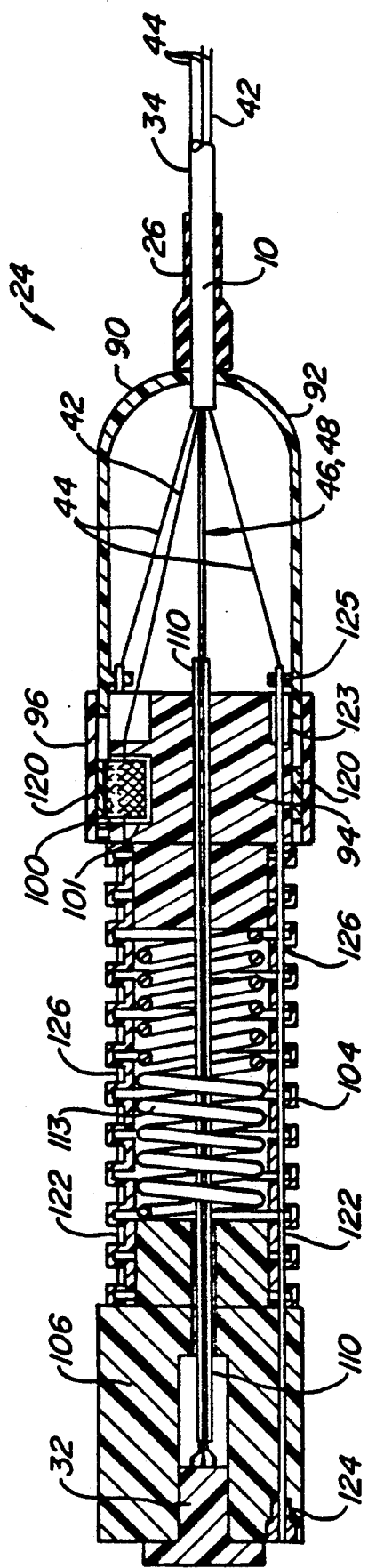
FIG. 9 is a side cross-sectional view of the shapable handle of the catheter of FIG. 1.

Referring now to FIG. 9, the shapable handle 24 of the steerable catheter 8 will now be described. Shaft 10 is mounted to the distal end 90 of handle 24 through strain relief 26. Outer jacket 34 of shaft 10 is fixed to handle 24 by heat or adhesive bonding, or other known means. Handle 24 is comprised of a nose cover 92, a distal frame member 94 adjacent nose cover 92, a torquer ring 96 disposed about a portion of distal frame member 94, a core wire retainer 100 disposed beneath the torquer ring 96 and received in a cavity 101 formed in the distal frame member 94, and convoluted tubing 104 extending between the distal frame member 94 and a proximal frame member 106. The convoluted tubing 104 may alternately be formed as a series of stacked disks, a gooseneck structure, or the like. The electrical connector 32 is secured to proximal end of proximal frame member 106. In addition, a bridge member 110, usually a nylon or polyethylene tube, extends between proximal frame member 106 and the distal frame 94 and is bonded at each end by adhesives or other means. Electrode wires 46 and thermocouple wires 48 extend from the connector 36 in proximal frame member 106 through bridge 110 to nose cover 92 and into shaft 10. A spring 113 is also disposed through the central bore 112 in order to enhance the hoop strength of the convoluted tube 104.

Core wire 42 enters nose cover 92 from shaft 10 and angles radially outward so as to mechanically couple with torquer ring 96. The proximal end of core wire 42 is fixed to core wire retainer 100, usually by extending through a center hole through core wire retainer 100 and being engaged by an adhesive or a set screw (not illustrated) extending radially inward. Core wire retainer 100 is cylindrical in shape and lies within a cavity 101 of torquer ring 96, such that turning torquer ring 96 rolls core wire retainer 100. Usually, the outer surface of core wire retainer 100 is knurled, and a friction pad 120 is disposed between core wire retainer and torquer ring 96, for improved contact therebetween. Other mechanisms for applying torque to the proximal end of core wire 42, of course, would also be available, such as rack and pinion systems where the interior surface of torquer ring 96 would have a gear surface to engage an exterior gear surface of retainer 100. It would also be possible for the retainer 100 to have a cross-sectional shape other than round, such as oval or elliptical, in order to transmit a variable force to the core wire 42. Thus, by rotating torquer ring 96, core wire retainer 100 is rotated, thereby applying a torque to the proximal end of core wire 42, where the torque will be transmitted to the distal tip section 16 of the catheter 8.

The relative diameters of the core wire retainer 100 and torque ring 96 will be selected to provide a particular ratio between ring rotation and wire rotation, usually being 1:4 (torquer ring:control wire). In this way, a small rotation of the torque ring 96 can cause a greater rotation of the proximal end of core wire 100. The ratio can be varied depending, for example, on the torsional stiffness of the core wire 100 and other variable factors.

Pull wires 44 enter the handle from shaft 10 and angle radially outward so as to pass through tubes 122. Tubes 122 are usually composed of stainless steel and extend through the distal frame member 94, the passages 126 in convoluted tube member 104 and to anchor points 124 at the proximal end of proximal frame member 106. Preferably, anchor points 124 comprise tensioning screws for adjusting the tension of pull wires 44. To provide controlled friction at the distal end of tubes 122 on the pull wires 44, sleeves 123 are received in holes in the distal face of distal frame member 94. Set screws 125 hold the sleeves 123 in place and can be used to increase friction by tightening. In this way, friction on the pull wires 44 can be adjusted to permit axial motion of the wires while the handle is being shaped, while holding the wires in place when the handle is not being shaped.

Figure 10:
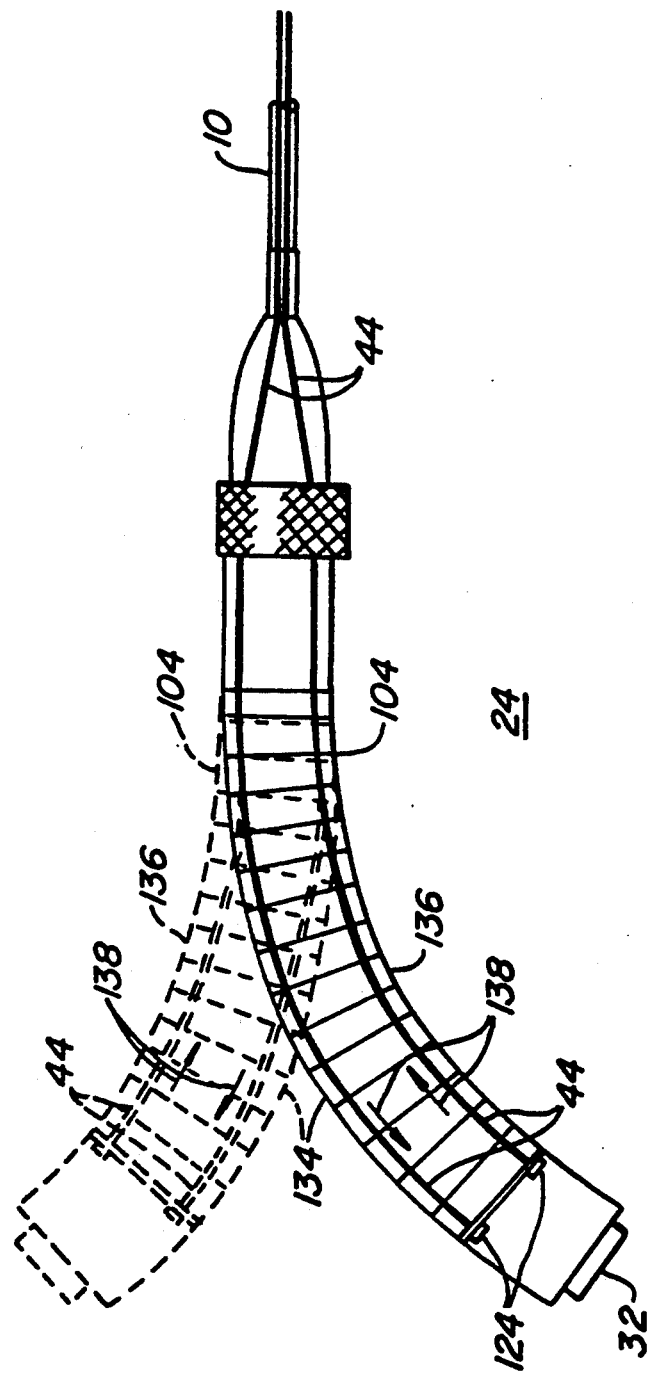
FIG. 10 is a schematic of the shapable handle of the catheter of FIG. 1.

Referring now to FIG. 10, convoluted tubing 104 is preferably nylon or other flexible material, and is configured to have alternating cylindrical segments of larger and smaller diameter such that the tubing is longitudinally expandable and contractible. This permits the convoluted tubing member 104 to be deflected laterally with respect to a distal portion. By such deflection, a lateral portion 134 of tubing member 104 at the outside of the bend becomes elongated, while the opposing lateral portion 136 at the inside of the bend is shortened. In this manner, pull wires 44 in tubes 122 are subject to tension or relaxation, depending upon in which lateral portion of tubing member 104 they are disposed, as shown by arrows 138.

Materials and dimensions of the convoluted tubing member or other shapable member are selected so as to provide sufficient flexibility for deflection, and to be "deformable," i.e. to be substantially non-resilient so as to remain in a deflected position when force is released from the handle. Convoluted tubing 104 may alternatively comprise a plurality of alternating disks of larger and smaller diameter on a bendable core of a soft, malleable material such as copper or brass.

With this construction, as shown in FIG. 10, lateral deflection of a proximal portion of handle 24 by bending convoluted tubing member 104 exerts a tensile force to the pull wires 44 at the outside portion 134 of the bend, while relaxing tension to pull wires at the inside portion 136 of the bend. Accordingly, at the distal end of the catheter, pull wires 44 brought into tension pull the distal end via anchor plate 72, with the opposing relaxed pull wires allowing the tube to deflect. The attachment of pull wires 44 to handle 24 may be configured so that a particular deflection of handle 24 produces deflection of distal tip of the catheter in a desired direction, either corresponding to or complementary to the direction of deflection of handle 24.

Figure 11:
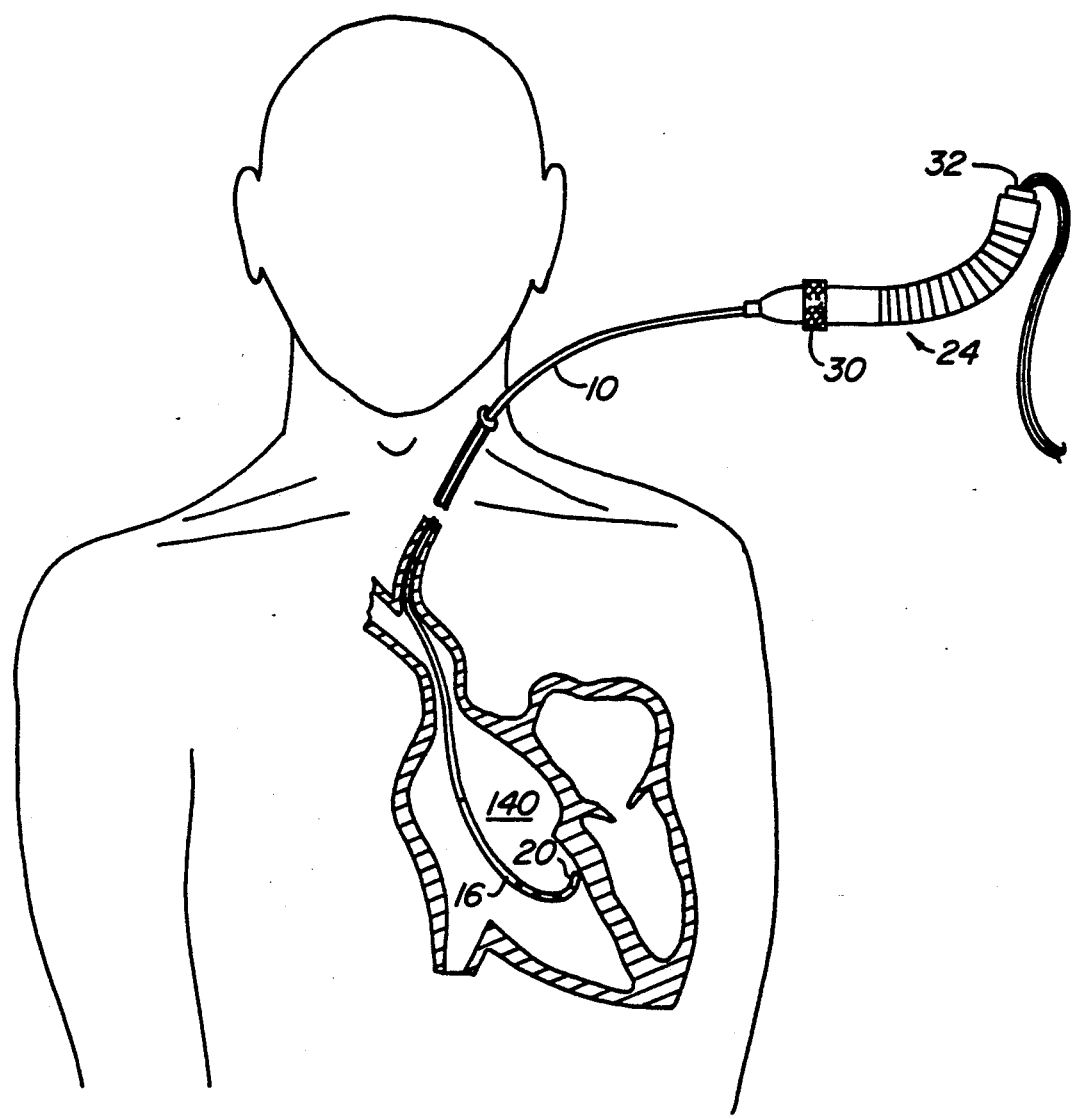
FIG. 11 is a schematic of the catheter of FIG. 1 positioned in the heart of a patient according to the principles of the present invention.

In the method of the present invention, an electrode is positioned within a chamber of the heart using the catheter shown in FIGS. 1-9. As illustrated in FIG. 11, the electrode 20, disposed at the distal end of the catheter as described above, is percutaneously introduced through a major vein or artery, such as the aorta, to the heart chamber 140. Electrode 20 may then be positioned near the target site on the interior wall of the heart chamber for ablation. This is accomplished by deflecting shapable handle 24 so as to produce a corresponding deflection in distal tip section 16. Further rough positioning can be achieved by rotating or twisting handle 24 such that the entire catheter assembly rotates, translating the rotational motion to tip section 16. Fine positioning is then accomplished by rotating torquer ring 30 on handle 24, which turns core wore 42, applying a torque to tip section 16. This provides precise and controllable rotational positioning of tip electrode 20 at the target site. Ablation may then be performed by applying RF energy to the target location through electrode 20, which is coupled to connector 32 via wires 46, connector 32 being connected to an RF power supply.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A steerable catheter comprising:
   a catheter shaft having a distal end, a proximal end, and a central lumen extending therebetween, wherein a distal portion of the shaft is deflectable;
   means extending from the proximal end to the distal end for deflecting a distal portion of the shaft about a transverse axis;
   a core wire extending through the central lumen and attached to the distal end of the shaft; and
   means for applying torque to a proximal end of the core wire to deflect the distal portion of the shaft about its longitudinal axis without deflecting the proximal portion of the shaft about its longitudinal axis.

2. A steerable catheter as in claim 1, further comprising at least one electrode at the distal end of the shaft, and means for connecting the electrode to an external radiofrequency generator.

3. A steerable catheter as in claim 2, further comprising at least one additional electrode disposed on the shaft and located proximally of the electrode disposed at the distal end, and means for connecting the additional electrode to external monitoring equipment.

4. A steerable catheter as in claim 1, wherein the means for deflecting the distal portion comprises at least three pull wires which are attached to radially offset locations at the distal end of the deflectable portion of the shaft, and means at the proximal end of the shaft for selectively applying tension to the pull wires to cause deflection of the deflectable portion.

5. A steerable catheter as in claim 4, wherein the distal portion of the shaft includes at least three radially offset lumens, and wherein the pull wires are disposed in the central lumen of the catheter shaft over a proximal portion thereof and disposed in the radially offset lumens over the distal portion thereof.

6. A steerable catheter as in claim 4, wherein the means for selectively applying tension comprises a shapeable handle, the shapeable handle including a proximal handle end and a distal handle end, the pull wires passing through the shapeable handle and terminating at the proximal handle end.

7. The steerable catheter as in claim 6 wherein the shapeable handle is constructed to assume a smoothly curved shape between its distal and proximal handle ends when said proximal handle end is deflected laterally relative to the distal handle end.

8. The steerable catheter as in claim 7 wherein the shapeable handle includes means for maintaining said smoothly curved shape until said proximal handle end is redeflected by a force external of said handle.

9. A steerable catheter comprising:
   a catheter shaft having a distal end, a proximal end, and a central lumen extending therebetween, wherein a distal portion of the shaft is deflectable;
   means extending from the proximal end to the distal end for deflecting a distal portion of the shaft about a transverse axis;
   a core wire extending through the central lumen and attached to the distal end of the shaft, the core wire being tapered to have a reduced diameter in the distal direction; and
   means for applying torque to a proximal end of the core wire to deflect the distal portion of the shaft about its longitudinal axis.

10. A steerable catheter comprising:
a catheter shaft having a distal end, a proximal end, and a central lumen extending therebetween, wherein a distal portion of the shaft is deflectable;
means extending from the proximal end to the distal end for deflecting a distal portion of the shaft about a transverse axis;
a core wire extending through the central lumen and attached to the distal end of the shaft; and
means for applying torque to a proximal end of the core wire to deflect the distal portion of the shaft about its longitudinal axis, the means for applying torque including a torquer ring rotatably mounted at the proximal end of the shaft and coupled to the core wire.

11. A steerable catheter comprising:
a catheter shaft having a distal end, a proximal end, and a central lumen extending therebetween;
a deflectable tip having a distal end, a proximal end, and a central lumen extending therebetween, wherein the proximal end of the deflectable tip is secured to the distal end of the catheter shaft;
a resilient and deflectable spring tube having a longitudinal lumen therethrough disposed coaxially in the central lumen of the deflectable tip, said spring tube extending from a point near the distal end of the deflectable tip and terminating near the proximal end of the deflectable tip;
at least three pull wires attached to radially offset locations at the distal end of the deflectable tip; and
means at the proximal end of the shaft for selectively applying tension to the pull wires for deflecting the tip about a transverse axis.

12. A steerable catheter as in claim 11, further comprising at least one electrode at the distal end of the deflectable tip, and means for connecting the electrode to an external radiofrequency generator.

13. A steerable catheter as in claim 12, further comprising at least one additional electrode disposed on the deflectable tip and located proximally of the electrode disposed at the distal end, and means for connecting the additional electrode to external monitoring equipment.

14. A steerable catheter as in claim 11, wherein the deflectable tip includes at least three radially offset lumens, and wherein the pull wires are disposed in the central lumen of the catheter and disposed in the radially offset lumen in the deflectable tip.

15. A steerable catheter as in claim 11, wherein the means for selectively applying tension comprises a shapable handle.

16. A steerable catheter as in claim 11, wherein the catheter shaft comprises a polymeric tube having a durometer in the range from 45D to 95D.

17. A steerable catheter as in claim 16, wherein the catheter shaft is reinforced with a braid or coil layer.

18. A steerable catheter as in claim 11, wherein the deflectable tip has a durometer in the range from 20A to 65D.

19. A steerable catheter comprising:
a catheter shaft having a distal end, a proximal end, and a central lumen extending therebetween;
a deflectable tip having a distal end, a proximal end, and a central lumen extending therebetween, wherein the proximal end of the deflectable tip is secured to the distal end of the catheter shaft;
a resilient and deflectable spring tube having a longitudinal lumen therethrough disposed coaxially in the central lumen of the deflectable tip, said spring tube extending from a point near the distal end of the deflectable tip and terminating near the proximal end of the deflectable tip, the spring tube including a polyimide cylinder which extends 1 cm to 3 cm into the central lumen of the catheter shaft; and
means extending from the proximal end of the catheter shaft to the distal end of the deflectable tip for deflecting the tip about a transverse axis.

20. A steerable catheter comprising:
a catheter shaft having a distal end, a proximal end, and a central lumen extending therebetween;
a deflectable tip having a distal end, a proximal end, and a central lumen extending therebetween, wherein the proximal end of the deflectable tip is secured to the distal end of the catheter shaft;
a spring tube disposed coaxially in the central lumen of the deflectable tip;
means extending from the proximal end of the catheter shaft to the distal end of the deflectable tip for deflecting the tip about a transverse axis;
a core wire extending through the central lumens of the catheter shaft and deflectable tip and attached to the distal end of the tip; and
means for applying torque to a proximal end of the core wire to deflect the deflectable tip about its longitudinal axis without deflecting the proximal portion of the catheter shaft about its longitudinal axis.

21. A steerable catheter as in claim 20, further comprising at least one electrode at the distal end of the deflectable tip, and means for connecting the electrode to an external radiofrequency generator.

22. A steerable catheter as in claim 21, further comprising at least one additional electrode disposed on the deflectable tip and located proximally at the electrode disposed at the distal end, and means for connecting the additional electrode to external monitoring equipment.

23. A steerable catheter as in claim 21 further comprising a temperature sensor at the distal end of the deflectable tip, and means for connecting the temperature sensor to temperature measurement equipment.

24. A steerable catheter as in claim 20, wherein the means for deflecting the deflectable tip comprises at least three pull wires which are attached to radially offset locations at the distal end of the deflectable tip, and means at the proximal end of the shaft for selectively applying tension to the pull wires to cause deflection of the deflectable tip.

25. A steerable catheter as in claim 24, wherein the deflectable tip includes at least three radially offset lumens, and wherein the pull wires are disposed in the central lumen of the catheter shaft and disposed in the radially offset lumens in the deflectable tip.

26. A steerable catheter as in claim 24, wherein the means for selectively applying tension comprises a shapable handle.

27. A steerable catheter as in claim 20, wherein the core wire is tapered to have a reduced diameter in the distal direction.

28. A steerable catheter as in claim 20, wherein the means for applying torque comprises a torquer ring rotatably mounted at the proximal end of the shaft and coupled to the core wire.

29. A steerable catheter as in claim 20, wherein the catheter shaft comprises a polymeric tube having a durometer in the range from 60D to 95D.

30. A steerable catheter as in claim 20, wherein the catheter shaft is reinforced with a braid or coil layer.

31. A steerable catheter as in claim 20, wherein the deflectable tip has a durometer in the range from 20A to 65D.

32. A steerable catheter comprising:
a catheter shaft having a distal end, a proximal end, and a central lumen extending therebetween;
a deflectable tip having a distal end, a proximal end, and a central lumen extending therebetween, wherein the proximal end of the deflectable tip is secured to the distal end of the catheter shaft;
a spring tube disposed coaxially in the central lumen of the deflectable tip, the spring tube including a polyimide cylinder which extends 1 cm to 3 cm into the central lumen of the catheter shaft;
means extending from the proximal end of the catheter shaft to the distal end of the deflectable tip for deflecting the tip about a transverse axis;
a core wire extending through the central lumens of the catheter shaft and deflectable tip and attached to the distal end of the tip; and
means for applying torque to a proximal end of the core wire to deflect the deflectable tip about its longitudinal axis.

33. A method for positioning an electrode within a heart chamber, said method comprising:
percutaneously introducing the distal end of a catheter through the aorta to the heart chamber, wherein the electrode is disposed at the distal end of the catheter;
deflecting the distal end of the catheter about a transverse axis by pulling on at least one pull wire attached to the distal end of the catheter to position the electrode near a target site on an interior wall of the heart chamber; and
applying rotational torque to a proximal end of a core wire independent of said pull wire which extends through a central lumen of the catheter and is attached to the distal end of the catheter, whereby the distal end of the catheter is deflected about a longitudinal axis to further position the electrode near the target site.

34. A method as in claim 33, further comprising applying radiofrequency energy to the target location through the electrode.

35. A steerable catheter comprising:
a catheter shaft having a distal end, a proximal end, and a central lumen extending therebetween;
a flexible distal tip section secured to the distal end of the shaft and having a central lumen coaxially aligned with the lumen of the shaft;
means extending from the proximal end of the shaft to the distal tip section for deflecting the distal tip section about a transverse axis;
an electrode disposed at the distal end of the distal tip; and
a tapered core wire extending from the lumen of the catheter shaft, through the lumen of the distal tip section, and to the electrode, whereby uniform bending of the distal tip is enhanced.

36. A steerable catheter as in claim 35, further comprising means for applying torque to a proximal end of the core wire to deflect the distal tip section about its longitudinal axis.

37. A steerable catheter as in claim 36, wherein the means for applying torque comprises a torquer ring rotatably mounted at the proximal end of the shaft and coupled to the core wire.

38. A steerable catheter as in claim 35, wherein the means for deflecting the distal portion comprises at least three pull wires which are attached to radially offset locations at the distal end of the deflectable portion of the shaft, and means at the proximal end of the shaft for selectively applying tension to the pull wires to cause deflection of the deflectable portion.

39. A steerable catheter as in claim 38, wherein the distal portion of the shaft includes at least three radially offset lumens, and wherein the pull wires are disposed in the central lumen of the catheter shaft over a proximal portion thereof and disposed in the radially offset lumens over the distal portion thereof.

40. A steerable catheter as in claim 38, wherein the means for selectively applying tension comprises a shapable handle.

41. A steerable catheter comprising:
a catheter shaft having a distal end, a proximal end, and a central lumen extending therebetween;
an electrode at the distal end of the shaft;
means extending from the proximal end to the distal end of the shaft for deflecting a distal portion about a transverse axis, wherein said means includes at least three pull wires which are attached to radially offset locations at the distal end of the deflectable portion of the shaft, and means at the proximal end of the shaft for selectively applying tension to the pull wires to cause deflection of the deflectable portion; and
an anchor plate secured between the distal end of the catheter shaft and the electrode, wherein said anchor plate receives the distal ends of the pull wires and is composed of an electrically and thermally insulating material.

42. A steerable catheter as in claim 41, wherein the distal portion of the shaft includes at least three radially offset lumens, and wherein the pull wires are disposed in the central lumen of the catheter shaft over a proximal portion thereof and disposed in the radially offset lumens over the distal portion thereof.

43. A steerable catheter as in claim 41, wherein the means for selectively applying tension comprises a shapable handle.

44. A steerable catheter as in claim 41, further comprising a core wire extending through the central lumen of the shaft and attached at the electrode.

45. A steerable catheter as in claim 44, further comprising means at the proximal end of the shaft for applying torque to the proximal end of the core wire to deflect the distal end of the shaft about its longitudinal axis.

46. A steerable catheter comprising:
a catheter shaft having a distal end, a proximal end, and a central lumen extending therebetween;
a deflectable tip having a distal end, a proximal end, and a central lumen extending therebetween, the deflectable tip including at least three radially offset lumens, wherein the proximal end of the deflectable tip is secured to the distal end of the catheter shaft;
a resilient spring tube disposed coaxially in the central lumen of the deflectable tip; and
means extending from the proximal end of the catheter shaft to the distal end of the deflectable tip for deflecting the tip about a transverse axis, said means for deflecting comprising at least three pull wires which are attached to radially offset locations at the distal end of the deflectable tip, and means at the proximal end of the shaft for selectively applying tension to the pull wires to cause deflection of the deflectable tip, wherein the pull wires are disposed in the central lumen of the catheter and disposed in the radially offset lumen in the deflectable tip.

47. A steerable catheter as in claim 46, wherein the means for selectively applying tension comprises a shapable handle.

48. A steerable catheter comprising:

a catheter shaft having a distal end, a proximal end, and a central lumen extending therebetween;

a deflectable tip having a distal end, a proximal end, and a central lumen extending therebetween, wherein the proximal end of the deflectable tip is secured to the distal end of the catheter shaft;

a resilient spring tube disposed coaxially in the central lumen of the deflectable tip, the spring tube comprising a polyimide cylinder which extends 1 cm to 3 cm into the central lumen of the catheter shaft; and means extending from the proximal end of the catheter shaft to the distal end of the deflectable tip for deflecting the tip about a transverse axis.

* * * * *